(12) United States Patent
Hecht et al.

(10) Patent No.: US 7,763,715 B2
(45) Date of Patent: Jul. 27, 2010

(54) EXTRACTING BIOPOLYMERS FROM A BIOMASS USING IONIC LIQUIDS

(75) Inventors: Stacie Ellen Hecht, West Chester, OH (US); Raymond Louis Niehoff, Hamilton, OH (US); Karunakaran Narasimhan, West Chester, OH (US); Charles William Neal, Fairfield, OH (US); Paul Arlen Forshey, Cincinnati, OH (US); Dean Van Phan, West Chester, OH (US); Anju Deepali Massey Brooker, Gosforth (GB); Katherine Helen Combs, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 574 days.

(21) Appl. No.: 11/406,620

(22) Filed: Apr. 19, 2006

(65) Prior Publication Data
US 2006/0241287 A1 Oct. 26, 2006

Related U.S. Application Data

(60) Provisional application No. 60/674,131, filed on Apr. 22, 2005.

(51) Int. Cl.
*C07K 14/78* (2006.01)
(52) U.S. Cl. ............... 530/357; 530/356; 528/480
(58) Field of Classification Search ............ 536/20; 530/356; 528/480
See application file for complete search history.

(56) References Cited

U.S. PATENT DOCUMENTS

| | | | |
|---|---|---|---|
| 1,943,176 A | 1/1934 | Graenacher | |
| 5,145,607 A | 9/1992 | Rich | |
| 5,565,421 A | 10/1996 | Aszman | |
| 5,821,299 A | 10/1998 | Noda | |
| 5,902,573 A * | 5/1999 | Kapral | 424/70.1 |
| 5,942,597 A | 8/1999 | Noda | |
| 6,225,438 B1 | 5/2001 | Green | |
| 6,228,997 B1 | 5/2001 | Akkara | |
| 6,297,203 B1 | 10/2001 | Gushey | |
| 6,723,689 B1 | 4/2004 | Hoang | |
| 6,790,822 B1 | 9/2004 | Baba et al. | |
| 6,808,557 B2 * | 10/2004 | Holbrey et al. | 106/163.01 |
| 6,824,599 B2 | 11/2004 | Swatloski | |
| 2003/0157351 A1 | 8/2003 | Swatlowski | |
| 2004/0077519 A1 | 4/2004 | Price et al. | |
| 2004/0097755 A1 | 5/2004 | Abbott | |
| 2004/0262578 A1 | 12/2004 | Wasserscheid et al. | |
| 2005/0288484 A1 * | 12/2005 | Holbrey et al. | 528/480 |

FOREIGN PATENT DOCUMENTS

| | | |
|---|---|---|
| JP | 20029003478 A2 | 1/2002 |
| JP | 2004175785 A2 | 6/2004 |
| WO | WO 2004/005286 A2 | 1/2004 |
| WO | WO 2005/017001 A1 | 2/2005 |
| WO | WO 2005/017252 A1 | 2/2005 |
| WO | WO 2005/023873 A1 | 3/2005 |

OTHER PUBLICATIONS

Rogers et al, Biomacromolecules, 2004, 5, 1379-1384.*
Levine et al, The Journal of Biological Chemistry, 1965, 240(6), 2284-89.*
Reichert, Derivatization of Chitin in Room Temperature Ionic Liquids, Department of Chemistry and Center for Green Manufacturing, The University of Alabama, Abstracts of Papers, 222 NDACS Mtg. Chicago, Illinois Aug. 26, 2001, American Chemical Society.
Spear, Ionic Liquids as Benign solvents for Extraction of Astaxanthin and Solubilization of Chitin, Center for Green Manufacturing, The University of Alabama, Abstracts of Papers, $221^{st}$ ACS National Meeting, San Diego, CA Apr. 1-5, 2001.
Reichert, Solubilization and Derivatization of Chitin in Room Temperature Ionic Liquids, Department of Chemistry and Center for Green Manufaturing, the University of Alabama, Abstracts of Papers, $221^{st}$ ACS National Meeting, San Diego, CA, Apr. 1-5, 2001.
Rogers, Non-sugar products from sugarcane for the new millennium: green pathways to a carbohydrate-economy, Center for Green Manufacturing, The University of Alabama, Publication of Technical Papers and Proceedings of the Annual Meeting of Sugar Industry Technologists, (2001), 60, 291-301.
Rogers, Green chemistry, the carbohydrate economy, and ionic liquids: Compatible goals, compatible chemistries, Abstracts of Papers—American Chemical Society (2001), $221^{st}$ IEC-347.
Spear, Solubility of mono-and di-saccharides in Ionic Liquids, Center for Green Manufacaturing, The University of Alabama, Abstracts of Papers—American Chemical Society (2001) $221^{st}$ IEC-053.
Reichert, Solubilization and derivatization of chitin in room temperature ionic liquids, Department of Chemistry and Center for Green Manufacturing, the University of Alabama, Abstracts of papers, American Chemical Society (2001) $221^{st}$ IEC-052.
Swatloski, Ionic liquids as green solvents for the dissolution and regeneration of cellulose, Department of Chemistry and Center for Green Manufacturing, The University of Alabama, Abstracts of Papers, $225^{th}$ ACS National Meeting, New Orleans, LA, US, Mar. 23-27, 2003.
Swatloski, Ionic liquids as green solvents: Engineering new biobased materials, Department of Chemistry and Center for Green Manufacturing, The University of Alabama, Abstracts of Papers, $226^{th}$ ACS National Meeting, Sep. 7-11, 2003.

(Continued)

*Primary Examiner*—Shaojia Anna Jiang
*Assistant Examiner*—Ganapathy Krishnan
(74) *Attorney, Agent, or Firm*—C. Brant Cook

(57) ABSTRACT

Methods for using ionic liquids to extract and separate a biopolymer from a biomass containing the biopolymer are disclosed. Methods for dissolving a biopolymer in an ionic liquid are also disclosed. A recovery solvent is used to reduce the solubility of the biopolymer in the ionic liquid and conventional separation techniques are used to recover the biopolymer. Biopolymers encompassed by this invention include chitin, chitosan, elastin, collagen, keratin and polyhydroxyalkanoate.

16 Claims, No Drawings

OTHER PUBLICATIONS

Rogers, CMPO-impregnated cellulosic materials from ionic liquids for f-element separations, Department of Chemistry and Center for Green Manufacturing, the University of Alabama, Abstracts of Papers, 226$^{th}$ ACS National Meeting, New York, NY, Sep. 7-11, 2003.

Swatloski, Properties of Regenerated cellulose from ionic liquids, Department of Chemistry and Center for Green Manufacturing, The University of Alabama, Abstracts of Papers, 225$^{th}$ ACS National Meeting, Mar. 23-27, 2003.

Swatloski, Ionic Liquids: New Solvents for Non-Derivitized Cellulose Dissolution, Department of Chemistry and Center for Green Manufacturing, The University of Alabama, Abstracts of Papers, 224$^{th}$ ACS National Meeting, Boston, MA, Aug. 18-22, 2002.

Swatloski, Dissolution of cellulose with ionic liquids, The University of Alabama, Journal of the American Chemical Society (2002), 124(18), 4974-4975.

Fan, Xiuling, Dissertation Abstract Value-Added Products From Chicken-Feather Fibers and Protein, May 10, 2008, Submitted to the Graduate Faculty of Auburn University, pp. 1-274.

* cited by examiner

EXTRACTING BIOPOLYMERS FROM A BIOMASS USING IONIC LIQUIDS

CROSS-REFERENCE TO RELATED APPLICATIONS

This application claims the benefit of U.S. Provisional Application Ser. No. 60/674,131, filed on Apr. 22, 2005.

FIELD OF THE INVENTION

The present invention relates to methods for using ionic liquids to extract and separate a biopolymer from a biomass containing the biopolymer. The present invention also relates to methods for dissolving a biopolymer in an ionic liquid. Biopolymers encompassed by this invention include chitin, chitosan, elastin, collagen, keratin and polyhydroxyalkanoate.

BACKGROUND OF THE INVENTION

Various synthetic polymers are typically produced from petro-chemical sources via well-known chemical processes. In recent years, the industry has renewed its focus on biopolymers from environmentally friendly, renewable sources of plants, animals and other living organisms. Extracting or separating the biopolymers from their natural sources often employs large quantities of volatile organic solvents or other undesirable chemical solvents. It is highly desirable to use a "green solvent" to extract and process biopolymers.

In recent years, ionic liquids have been extensively evaluated as environmental-friendly or "green" alternatives to conventional organic solvents. Generally speaking, ionic liquids refer to a specific class of molten salts which are liquids at temperatures of 100° C. or below. Ionic liquids have very low vapor pressure and generate virtually no hazardous vapors. Moreover, ionic liquids are composed of charged species, which provide a highly polar medium useful in various applications, such as extraction, separation, catalysis and chemical synthesis medium.

Ionic liquids have been used to dissolve or treat cellulosic materials and starch. Such applications are described in U.S. Pat. No. 1,943,176; U.S. Pat. No. 6,824,599; WO 05/29329; WO 05/17001; WO 05/17252; and WO 05/23873.

It has now been found that other biopolymers can be dissolved in ionic liquids. It has also been found that other biopolymers can be extracted or separated from their natural biological sources using ionic liquids. It is surprising to find that certain biopolymers that are insoluble or have very limited solubility in water or organic solvents can be dissolved in ionic liquids, and extracted from their biological sources with ionic liquids.

SUMMARY OF THE INVENTION

The present invention relates to a method for dissolving biopolymers comprising mixing a biopolymer with an ionic liquid in its fluid state and in the substantial absence of water to form a mixture, wherein the biopolymer is chitin, chitosan, elastin, collagen, keratin or polyhydroxyalkanoate.

The present invention also relates to a method for separating a biopolymer from a biomass comprising the biopolymer and additional materials that are insoluble in certain ionic liquids; the method comprises the steps of mixing the biomass with an ionic liquid in its fluid state and in the substantial absence of water to form a mixture; and removing the insoluble additional material, thereby producing a substantially anhydrous composition (i.e., a recoverable composition) comprising the ionic liquid and the biopolymer; wherein the biopolymer is chitin, chitosan, elastin, collagen, keratin or polyhydroxyalkanoate.

The present invention further relates to a method for extracting a biopolymer from a biomass containing the biopolymer; the method comprises the step of contacting the biomass with an ionic liquid in its fluid state and in the substantial absence of water, wherein the biopolymer is chitin, chitosan, elastin, collagen, keratin or polyhydroxyalkanoate.

The present invention also encompasses compositions comprising a biopolymer and an ionic liquid obtained by any of the methods disclosed herein.

DETAILED DESCRIPTION OF THE INVENTION

The term "biomass" as used herein refers to the natural and biological sources containing biopolymers and from which the biopolymers can be extracted or separated by the ionic liquid processes of the present invention.

The term "biopolymers" as used herein refers to chitin, chitosan, elastin, collagen, keratin and polyhydroxyalkanoate.

The terms "substantial absence" and "substantially anhydrous" as used herein mean less than about 5 weight % of water is present. In some embodiments, less than 1 wt % water is present.

Ionic Liquids

The term "ionic liquid" as used herein refers to a salt that has a melting temperature of about 100° C. or less, alternatively of about 60° C. or less, or in a further alternative, of about 40° C. or less. Some ionic liquids exhibit no discernible melting point (based on DSC analysis) but are "flowable" at a temperature of about 100° C. or below; other ionic liquids are "flowable" at temperatures from about 20 to about 80° C. As used herein, the term "flowable" means that the ionic liquid exhibits a viscosity of less than about 10,000 mPa·s at temperatures of about 100° C. or below or from about 20 to about 80° C. Thus, the "fluid state" of an ionic liquid is meant to encompass all of these embodiments, including the molten state and the flowable state.

It should be understood that the terms "ionic liquid", "ionic compound", and "IL" refer to ionic liquids, ionic liquid composites, and mixtures (or cocktails) of ionic liquids. The ionic liquid can comprise an anionic IL component and a cationic IL component. When the ionic liquid is in its fluid state, these components may freely associate with one another (i.e., in a scramble). As used herein, the term "cocktail of ionic liquids" refers to a mixture of two or more, preferably at least three, different and charged IL components, wherein at least one IL component is cationic and at least one IL component is anionic. Thus, the pairing of these three cationic and anionic IL components in a cocktail would result in at least two different ionic liquids. The cocktails of ionic liquids may be prepared either by mixing individual ionic liquids having different IL components, or by preparing them via combinatorial chemistry. Such combinations and their preparation are discussed in further detail in U.S. 2004/0077519A1 and U.S. 2004/0097755A1. As used herein, the term "ionic liquid composite" refers to a mixture of a salt (which can be solid at room temperature) with a proton donor Z (which can be a liquid or a solid) as described in the references immediately above. Upon mixing, these components turn into an ionic liquid that melts or flows at about 100° C. or less, and the mixture behaves like an ionic liquid.

The ionic liquid useful in the present invention comprises a cationic component having the following formula:

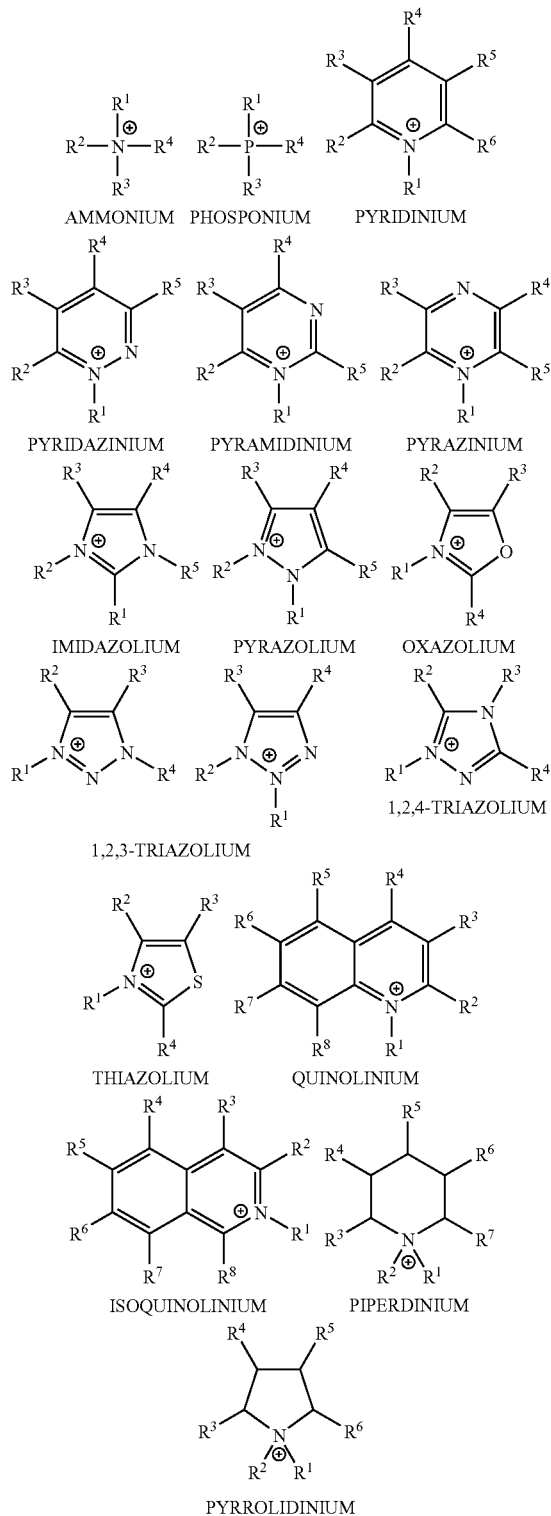

wherein $R^1$-$R^8$ are independently selected from the group consisting of C1-C6 alkyl, alkenyl, hydroxyalkyl, haloalkyl, alkoxylalkyl; C6-C10 aryl or C8-C16 alkylenearyl; and mixtures thereof.

The ionic liquid useful in the present invention comprises an anionic component, which when paired with the cationic component forms an ionic liquid. The anionic component is selected from the group consisting of halides, C1-C6 carboxylates, C1-C6 alkyl sulfates, mono- or di-C1-C10 alkyl sulfosuccinates, mono- or di-C1-C10 ester sulfosuccinates, and mixtures thereof.

In some embodiments, the ionic liquid has the formula:

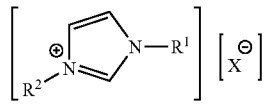

wherein $R^1$-$R^2$ are independently C1-C6 alkyl, alkenyl, hydroxyalkyl, haloalkyl, alkoxylalkyl; C6-C10 aryl or C8-C16 alkylenearyl; preferably a C1-C6 alkyl moiety or a C1-C6 alkoxyalkyl moiety; and the anionic component X is a halide or a C1-C6 alkyl, alkenyl, hydroxyalkyl, or haloalkyl moiety. In a specific embodiment, the ionic liquid has the formula immediately above, wherein $R^1$ is a C1-C6 alkyl moiety or C1-C6 alkoxyalkyl moiety, $R^2$ is methyl and the anion is chloride.

In other embodiments, the ionic liquid has the formula:

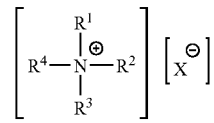

wherein $R^1$-$R^4$ are independently C1-C6 alkyl, alkenyl, hydroxyalkyl, haloalkyl, alkoxylalkyl; C6-C10 aryl or C8-C16 alkylenearyl; and the anionic component X is a halide or a C1-C6 alkyl, alkenyl, hydroxyalkyl, or haloalkyl. In still other embodiments, the ionic liquid has a dioctyl sulfosuccinate anion and a cationic component as shown immediately above.

Biopolymers

"Chitin" is a glucosamine polysaccharide having the general structure:

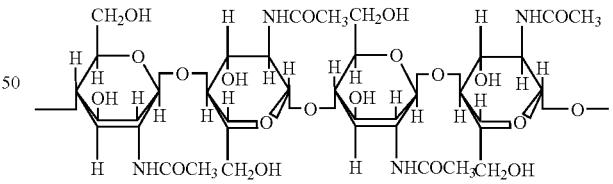

Sources containing chitin and from which chitin can be extracted include, but are not limited to, the hard outer shells of crustaceans, insects and other invertebrates; common examples include crabs, lobsters, beetles. Suitable biomass sources are also available from fungi, algae and yeasts.

"Chitosan" is the deacylated derivative of chitin. Sources containing chitosan and from which chitosan can be extracted include, but are not limited to, cell walls of fungi. Chitosan can also be produced from chitin pursuant to methods described, for example, in U.S. 2004/0215005 A1.

"Collagen" is the most abundant protein in multicellular animals. It is rich in proline and hydroxyproline. The molecule has a structure similar to a three-strand rope, in which each strand is a polypeptide chain. Collagen molecules assemble to form loose networks, or thick fibrils arranged in bundles or sheets. As collagen ages, it becomes more cross-linked and less hygroscopic. "Elastin" is a scleroprotein. Elastin molecules assemble to form a water insoluble, fibrous mass. These proteins are typically found in the connective tissues of human and animals. Sources containing collagen or elastin include but are not limited to skin, muscles, tendons, cartilages, blood vessels, bones and teeth.

"Keratins" encompass a class of natural fibrous proteins, typically comprising a high content of several amino acids, such as cysteine, arginine and serine; the cysteine units may form crosslinks via disulfide bonds. Depending on the extent of crosslinks, keratins range from soft types, such as the outer layers of skin, to the hard types, such as nails.

Sources containing keratins and from which keratins can be extracted include, but are not limited to, the external layers of skin, wool, hair and feathers, as well as nails, claws and hoofs. These source materials are produced by vertebrate animals and human.

"Polyhydroxyalkanoate" and "PHA" is a polymer comprising the following repeating unit:

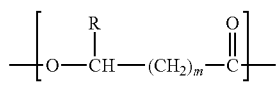

wherein R is preferably H, alkyl or alkenyl; and m is from about 1 to about 4. The terms polyhydroxyalkanoate and PHA include copolymers containing one or more different repeating units. For example, PHA copolymers may comprise at least two randomly repeating monomer units, wherein the first randomly repeating monomer unit has the structure

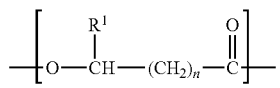

wherein $R^1$ is H, or $C_1$ to $C_2$ alkyl; and n is 1 or 2; the second randomly repeating monomer unit has the structure

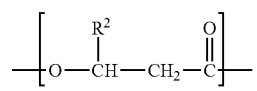

wherein $R^2$ is $C_3$ to $C_{19}$ alkyl or $C_3$ to $C_{19}$ alkenyl; and wherein at least 50% of the randomly repeating monomer units have the structure of the first randomly repeating monomer unit.

Other embodiments of PHA copolymers may contain hydroxybutyrate units, hydroxyhexanoate units, or mixtures thereof. Still other embodiments of PHA copolymers may contain 3-hydroxyproprionate, 3-hydroxybutyrate, 3-hydroxyvalerate, 3-hydroxyhexanoate, 3-hydroxyheptanoate, 3-hydroxyoctanoate, and mixtures thereof.

Sources containing PHA and from which PHA can be extracted include single-cell organisms such as bacteria or fungi and higher organisms such as plants. Suitable sources may be wild, farmed, cultivate or fermented.

Plants useful in the present invention include any genetically engineered plant designed to produce PHA. Preferred plants include agricultural crops such as cereal grains, oilseeds and tuber plants; more preferably, avocado, barley, beets, broad bean, buckwheat, carrot, coconut, copra, corn (maize), cottonseed, gourd, lentils, lima bean, millet, mung bean, oat, oilpalm, peas, peanut, potato, pumpkin, rapeseed (e.g., canola), rice, sorghum, soybean, sugarbeet, sugar cane, sunflower, sweet potato, tobacco, wheat, and yam. Such genetically altered fruit-bearing plants useful in the process of the present invention include, but are not limited to, apple, apricot, banana, cantaloupe, cherries, grapes, kumquat, lemon, lime, orange, papaya, peaches, pear, pineapple, tangerines, tomato, and watermelon. For example, the plants can be genetically engineered to produce PHA pursuant to the methods disclosed in Poirier, Y., D. E. Dennis, K. Klomparens and C. Somerville, "Polyhydroxybutyrate, a biodegradable thermoplastic, produced in transgenic plants", SCIENCE, Vol. 256, pp. 520-523 (1992); U.S. Pat. No. 5,610,041 and U.S. Pat. No. 5,650,555, both to Somerville et al. The following plants are particularly desirable to be genetically engineered to produce PHA because they can be agriculturally produced in abundance: soybean, potato, corn and coconut.

Suitable source is also available from bacteria which naturally produce PHA as well as genetically manipulated species specifically designed to produce a specific PHA of interest to the grower. Such genetically manipulated organisms are produced by incorporating the genetic information necessary to produce one or more types of PHA into the organisms. Typically, such genetic information is derived from bacteria which naturally produce PHA. Examples of such bacteria include those disclosed in NOVEL BIODEGRADABLE MICROBIAL POLYMERS, E. A. Dawes, ed., NATO ASI Series, Series E: Applied Sciences—Vol. 186, Kluwer Academic Publishers (1990); U.S. Pat. No. 5,292,860, Shiotani and Kobayashi, issued Mar. 8, 1994; U.S. Pat. No. 5,250,430, Peoples and Sinskey, issued Oct. 5, 1993; U.S. Pat. No. 5,245,023, Peoples and Sinskey, issued Sep. 14, 1993; U.S. Pat. No. 5,229,279, Peoples and Sinskey, issued Jul. 20, 1993.

An efficient production of PHA from plant oils by *Alcaligenes eutrophus* and its recombinant strain via a fermentation process is disclosed U.S. Pat. No. 6,225,438. Biomass containing PHA copolymers with short to medium chain of 3-hydroxyacyl monomers and C6, C7 and/or C8 3-hydroxyacxyl monomers can be produced by this fermentation process.

Processes

The present invention encompasses a method for dissolving biopolymers in ionic liquids in its fluid state and in the substantial absence of water. Due to the strong solvating power of the ionic liquid, biopolymers that are insoluble or have limited solubility in organic solvents or water can be dissolved under fairly mild conditions. The dissolution process can be carried out at temperatures from about room temperature (20° C.) to about 100° C. under atmospheric pressure. In some embodiments, the dissolution processes are carried out at temperatures from about 40 to about 90° C. Optionally, higher temperatures (for example, up to about 130° C.) may be employed to increase the dissolution rate, thus, reduce the processing time.

The dissolution step may take from about 1 minute to about 5 hours, depending on the temperature. The dissolution step produces a clear, transparent, or translucent solution which comprises the ionic liquid and the biopolymer. In a typical embodiment, from about 1% to about 50% by weight of the solution is the biopolymer. In other embodiments, the solution comprises from about 5% to about 45%, or from about 10% to about 40%, by weight of the solution of the biopolymer.

Gentle heating, agitation, sonication, pressure, radiation energy (e.g., microwave, infrared) may be applied to accelerate the dissolution of biopolymers, thereby reducing the processing time. Typically, it is not necessary to use acid or base additives to facilitate the dissolution. However, acid or base can optionally be added.

The method may further comprise the step of recovering the biopolymers from the solution by adding an effective amount of a non-solvent. A non-solvent is added to the biopolymer/IL mixture to change or weaken the solvating power of the ionic liquid, or to the processing time. Typically, it is not necessary to use acid or base additives to facilitate the dissolution. However, acid or base can optionally be added.

The method may further comprise the step of recovering the biopolymers from the solution by adding an effective amount of a recovery solvent. A recovery solvent is added to the biopolymer/IL mixture to change or weaken the solvating power of the ionic liquid, or to reduce the solubility of the biopolymer in the ionic liquid. The biopolymer can then be recovered by known separation methods, such as sedimentation, crystallization, centrifugation, decantation, filtration, and combinations thereof.

In one embodiment, an effective amount of recovery solvent is added to the biopolymer/IL mixture such that the biopolymer precipitates from the mixture. The weight ratio of recovery solvent to ionic liquid ranges from about 100:1 to about 1:2, preferably from about 20:1 to about 1:1, more preferably from about 10:1 to about 2:1. Optionally, acid or base can be added to the mixture to facilitate the precipitation and recovery of the biopolymers.

Exemplary recovery solvents include water, C1-C6 alcohols, C2-C6 ethers and acetone. Using water as the recovery solvent is particularly advantages because no volatile organic solvent is involved and the entire process is conducted with environmentally friendly substances.

After the separation of biopolymers, the recovery solvent can be separated from the ionic liquid by distillation or drying over absorbents, the latter is quite useful when water is the recovery solvent. Suitable absorbents or absorbent materials are those materials capable of selectively ingesting (via absorption or adsorption) water without ingesting ionic liquid. Suitable absorbents include, but are not limited to, hydrogel forming absorbent polymers, absorbent gelling materials (AGMs), and mixtures thereof. Exemplary absorbent materials are disclosed in U.S. Pat. No. 4,076,663; U.S. Pat. No. 4,734,478; U.S. Pat. No. 4,555,344; U.S. Pat. No. 4,828,710; U.S. Pat. No. 5,601,542; U.S. Pat. No. 6,121,509; WO 99/34841; and EP 648,521 A2.

The present invention also encompasses a process for separating a biopolymer from a biomass containing the biopolymer. The process comprises the steps of mixing the biomass with an ionic liquid in its fluid state and in the substantial absence of water to dissolve or extract the biopolymer from the biomass, and removing insoluble materials of the biomass, thereby producing a substantially anhydrous composition comprising the ionic liquid and the biopolymer. The weight ratio of ionic liquid to biomass in the mixing step ranges from about 20:1 to 1:200, preferably from about 10:1 to about 1:10, and more preferably from about 5:1 to about 1:5.

The mixing step may take from about 10 minutes to about 24 hours, preferably from about 30 minutes to about 10 hours, more preferably from about 1 hour to about 5 hours, in order to allow the biopolymer to dissolve in the ionic liquid.

Gentle heating and/or agitation may be applied to accelerate the dissolution of biopolymers, thereby reducing the processing time. Typical processing temperature ranges from about room temperature (20° C.) to about 130° C. In some embodiments, a processing temperature of about 40° C. to about 100° C. is used to dissolve the biopolymer; in other embodiments, a processing temperature of about 60° C. to about 95° C. is used to dissolve the biopolymer. Reducing the particle size of the biomass (e.g., by milling, pulverization, grinding) prior to subjecting the biomass to the process of the present invention also reduces the processing time. Pressure, agitation, sonication and radiation energy (e.g., microwave, infrared) may also be applied to reduce the processing time.

The process further comprises the step of adding an effective amount of nonsovlent to the substantially anhydrous composition to reduce the solubility of the biopolymer in the ionic liquid, thereby converting the composition into a recoverable composition. The weight ratio of recovery solvent to ionic liquid in the recoverable composition ranges from about 100:1 to about 1:2, preferably from about 20:1 to about 1:1, more preferably from about 10:1 to about 2:1. Optionally, acid or base can be added to facilitate the recovery of the biopolymer. The biopolymer can be easily separated from the recoverable composition by known separation methods, such as centrifugation, sedimentation, crystallization, decantation, filtration, and combinations thereof.

The amount of the biopolymer recovered by this process ranges from about 0.1% to about 50%, preferably from about 1% to about 25%, more preferably from about 3% to about 10%, by weight of the biomass.

The present invention further encompasses a process for extracting a biopolymer from a biomass containing the biopolymer. The process comprises the step of contacting the biomass with an ionic liquid in its fluid state and in the substantial absence of water. The extraction can be carried out in the batch extraction method or in the flow through stripping method. The weight ratio of total amount of ionic liquid used in the process to biomass ranges from about 20:1 to 1:200, preferably from about 10:1 to about 1:10, and more preferably from about 5:1 to about 1:5. The biopolymer can be recovered from the ionic liquid using recovery solvents followed by conventional separation methods, as described hereinabove.

EXAMPLES

Example 1

Polyhydroxyalkanoate (PHA) Dissolution 0.12 grams of PHA, a poly(hydroxybutyrate/hydroxyhexanoate) copolymer containing about 6 mol % hexanoate, is added to a glass vial containing 2 g of Terrasail® (available from Sachem, Inc.), which is a liquid at room temperature. The temperature of the vial is maintained at 115° C. for 3 minutes. The vial is agitated to enhance dissolution. A viscous, visually clear solution of polyhydroxyalkanoate in the ionic liquid is obtained.

Example 2

Keratin Dissolution and Recovery

Keratin (0.48 g) is added to a glass vial containing 3 g of 1-ethyl-3-methylimidazolium acetate (available from BASF), which is a liquid at room temperature. The temperature of the vial is maintained at 95° C. for 10 minutes in an oil bath. The vial is agitated to facilitate dissolution. A viscous, visually clear solution of keratin in the ionic liquid is obtained. The keratin-ionic liquid solution is poured into 150 mL of water. The pH of the mixture is then adjusted to pH 4.5 using 1N HCl; keratin precipitates from the mixture resulting in a cloudy solution. The resulting solution is filtered to recover the precipitated keratin.

Example 3

Extraction of PHA From a Biomass 60 g of a biomass, made via fermentation process using genetically engineered organism sample, containing a PHA, poly(3-hydroxybutyrate-co-3-hydroxyhexanoate) as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for dissolving biopolymers comprising mixing a biopolymer with an ionic liquid in its fluid state and in the substantial absence of water to form a mixture, wherein the biopolymer is keratin.

2. The method according to claim 1 wherein the ionic liquid contains a cationic component having the formula:

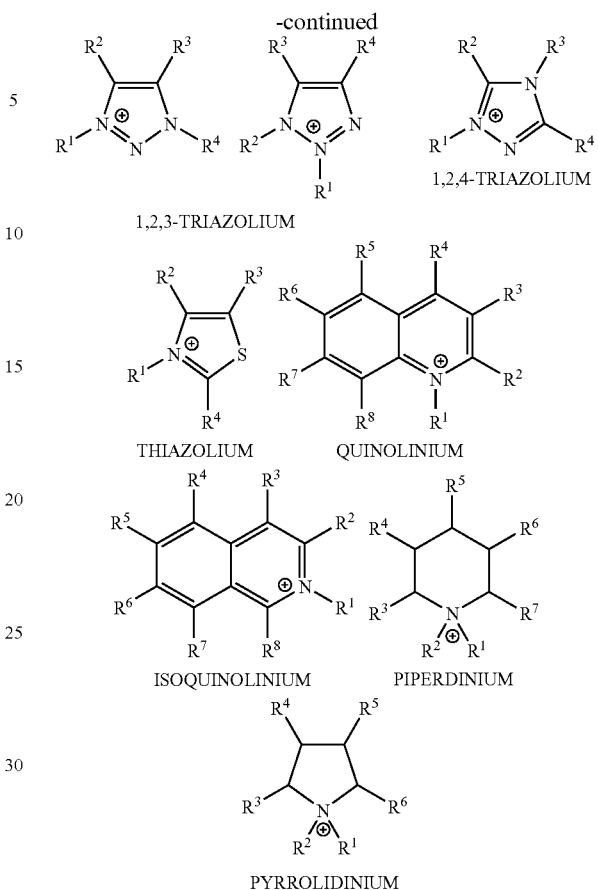

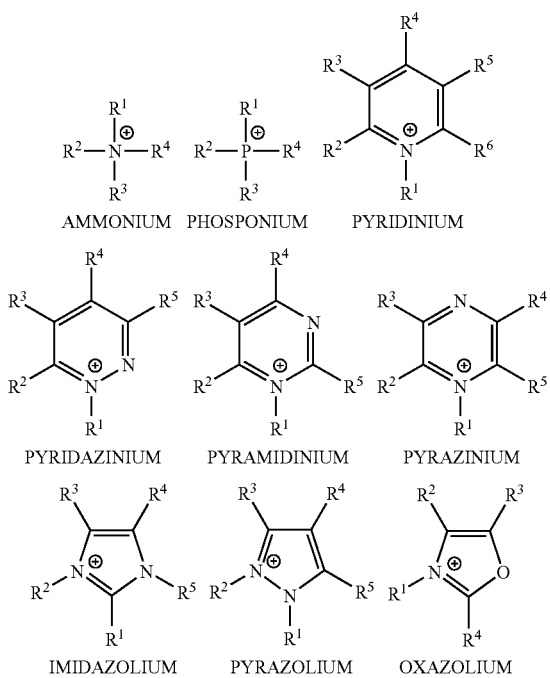

wherein $R^1$-$R^8$ are independently selected from the group consisting of C1-C6 alkyl, alkenyl, hydroxyalkyl, haloalkyl, alkoxylalkyl; C6-C10 aryl or C8-C16 alkylenearyl; and mixtures thereof.

3. The method according to claim 2 wherein the ionic liquid contains an anionic component selected from the group consisting of halides, C1-C6 carboxylates, C1-C6 alkyl sulfates, mono- or di-C1-C10-alkyl sulfosuccinates, mono- or di-C1-C10 ester sulfosuccinates, and mixtures thereof.

4. The method according to claim 1 further comprising the step of adding a recovery solvent to the mixture, wherein the recovery solvent is selected from the group consisting of water, C1-C6 alcohols, C2-C6 ethers, acetone, and mixtures thereof.

5. A composition produced by the method according to claim 1.

6. The composition comprising keratin and the ionic liquid according to claim 5 wherein the composition comprises, based on total composition weight, from about 5% to about 50% of keratin.

7. A method for separating a biopolymer from a biomass containing the biopolymer comprising the steps of mixing the biomass with an ionic liquid in its fluid state and in the substantial absence of water to form a mixture; and removing insoluble material, thereby producing a substantially anhydrous composition comprising the ionic liquid and the biopolymer; wherein the biopolymer is keratin.

8. The method according to claim 7 wherein the ionic liquid contains a cationic component having the formula:

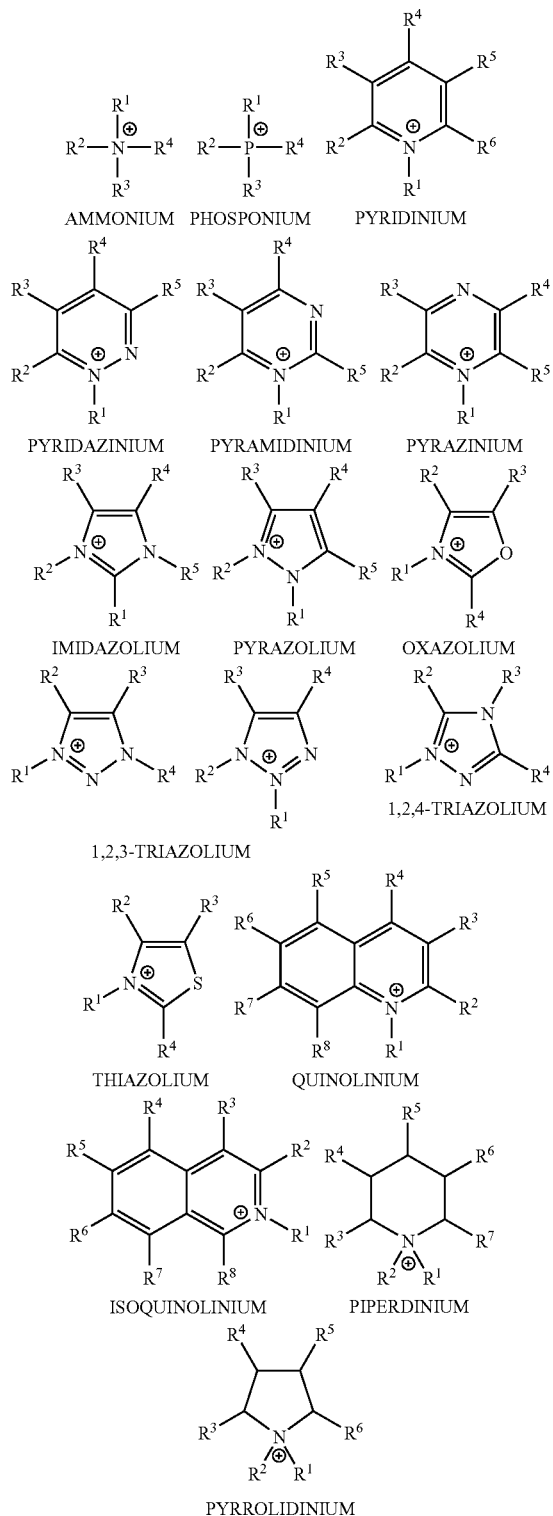

9. The method according to claim 7 wherein the ionic liquid contains an anionic component selected from the group consisting of halides, C1-C6 carboxylates, C1-C6 alkyl sulfates, mono- or di-C1-C10 alkyl sulfosuccinates, mono- or di-C1-C10 ester sulfosuccinates, and mixtures thereof.

10. The method according to claim 7 further comprising the step of adding a recovery solvent to the substantially anhydrous composition, thereby converting it into a recoverable composition.

11. The method according to claim 10 wherein the recovery solvent is selected from the group consisting of water, C1-C6 alcohols, C2-C6 ethers, acetone, and mixtures thereof.

12. The method according to claim 10 wherein weight ratio of recovery solvent:ionic liquid ranges from about 100:1 to 1:2.

13. The method according to claim 10 further comprising the step of separating the biopolymer from the recoverable composition.

14. The method according to claim 13 wherein the separating step is selected from the group consisting of centrifugation, sedimentation, crystallization, decantation, filtration, and combinations thereof.

15. A method for extracting a biopolymer from a biomass containing the biopolymer comprising the step of contacting the biomass with an ionic liquid in its fluid state and in the substantial absence of water, and extracting the biopolymer from the biomass, wherein the biopolymer is keratin.

16. The method according to claim 15 wherein the ionic liquid contains a cationic component having the formula:

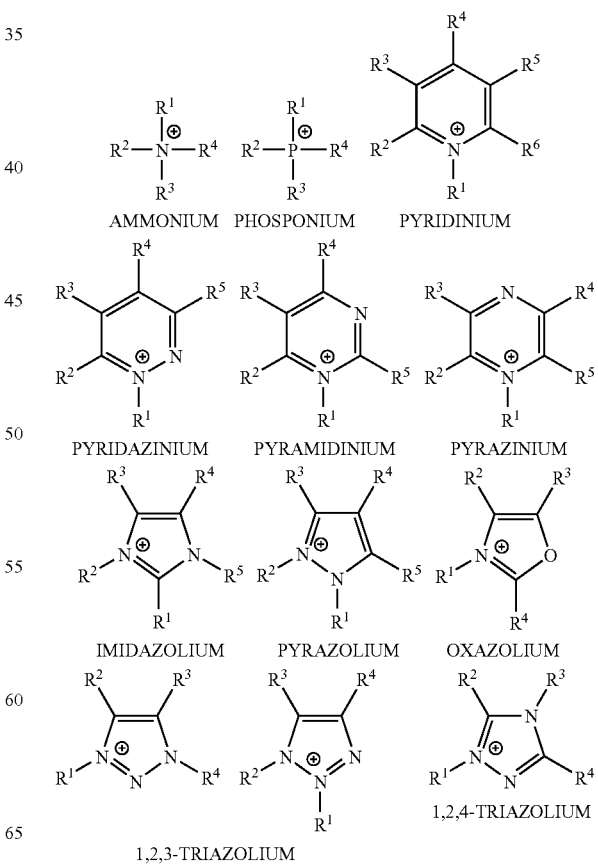

wherein $R^1$-$R^8$ are independently selected from the group consisting of C1-C6 alkyl, alkenyl, hydroxyalkyl, haloalkyl, alkoxylalkyl; C6-C10 aryl or C8-C16 alkylenearyl; and mixtures thereof.

-continued

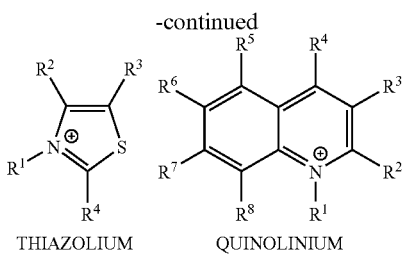

THIAZOLIUM   QUINOLINIUM

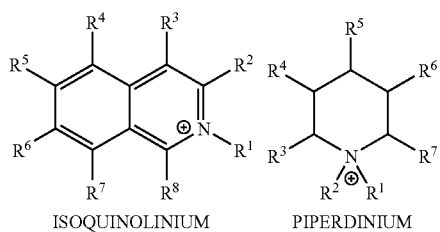

ISOQUINOLINIUM   PIPERDINIUM

-continued

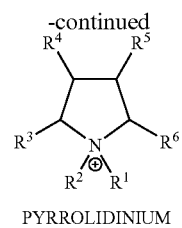

PYRROLIDINIUM wherein $R^1$-$R^8$ are independently selected from the group consisting of C1-C6 alkyl, alkenyl, hydroxyalkyl, haloalkyl, alkoxylalkyl; C6-C10 aryl or C8-C16 alkylenearyl; and mixtures thereof; and an anionic component selected from the group consisting of halides, C1-C6 carboxylates, C1-C6 alkyl sulfates, mono- or di-C1-C10 alkyl sulfosuccinates, mono- or di-C1-C10 ester sulfosuccinates, and mixtures thereof.

* * * * *